US012423812B2

(12) United States Patent
Sasuga

(10) Patent No.: US 12,423,812 B2
(45) Date of Patent: Sep. 23, 2025

(54) INFORMATION PROCESSING APPARATUS, INFORMATION PROCESSING METHOD, AND NON-TRANSITORY COMPUTER-READABLE STORAGE MEDIUM FOR TRAINING AN ESTIMATION MODEL SUCH THAT A LOSS IS REDUCED

(71) Applicant: FUJIFILM Corporation, Tokyo (JP)

(72) Inventor: Saeko Sasuga, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 360 days.

(21) Appl. No.: 18/186,954

(22) Filed: Mar. 21, 2023

(65) Prior Publication Data
US 2023/0230247 A1 Jul. 20, 2023

Related U.S. Application Data

(63) Continuation of application No. PCT/JP2021/027590, filed on Jul. 26, 2021.

(30) Foreign Application Priority Data

Sep. 29, 2020 (JP) .................................. 2020-163872

(51) Int. Cl.
*G06T 7/00* (2017.01)
*G06T 7/12* (2017.01)
(Continued)

(52) U.S. Cl.
CPC .................. *G06T 7/12* (2017.01); *G06T 7/62* (2017.01); *G06V 10/25* (2022.01); *G06V 10/758* (2022.01);
(Continued)

(58) Field of Classification Search
CPC .................. G06T 7/0012; G06T 7/62; G06T 2207/20081; G06T 2207/30096;
(Continued)

(56) References Cited

U.S. PATENT DOCUMENTS

2016/0063720 A1  3/2016  Han et al.
2017/0322950 A1  11/2017  Han et al.
(Continued)

FOREIGN PATENT DOCUMENTS

JP   2011141202   7/2011
JP   2017532092   11/2017
(Continued)

OTHER PUBLICATIONS

George Papandreou; et al., "Weakly- and Semi-Supervised Learning of a DCNN for Semantic Image Segmentation," arXiv:1502.02734v3, Oct. 5, 2015, pp. 1-13.
(Continued)

*Primary Examiner* — Siamak Harandi
(74) *Attorney, Agent, or Firm* — JCIPRNET

(57) ABSTRACT

A processor acquires a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images. The processor calculates, for each first training image, a first evaluation value for training an estimation model such that the plurality of regions specified by using the estimation model match the area information. The processor derives, for each second training image, estimation information in which the relationship indicated by the relationship information is estimated by using the estimation model to calculate a second evaluation value indicating a degree of deviation between the estimation information and the relationship information. The processor trains the estimation model such that a loss including,
(Continued)

as elements, the first evaluation value and the second evaluation value is reduced.

15 Claims, 12 Drawing Sheets

(51) Int. Cl.
*G06T 7/62* (2017.01)
*G06V 10/25* (2022.01)
*G06V 10/74* (2022.01)
*G06V 10/75* (2022.01)

(52) U.S. Cl.
CPC .. *G06V 10/761* (2022.01); *G06T 2207/20081* (2013.01); *G06T 2207/30096* (2013.01)

(58) Field of Classification Search
CPC . G06T 2207/10072; G06T 2207/20084; G06T 7/11; G06V 10/25; G06V 10/758; G06V 10/761; G06V 10/26; G06V 2201/031; G06V 10/764; A61B 6/03
See application file for complete search history.

(56) References Cited

U.S. PATENT DOCUMENTS

| | | |
|---|---|---|
| 2018/0068564 A1 | 3/2018 | Tanigawa et al. |
| 2019/0228264 A1 | 7/2019 | Huang et al. |
| 2019/0278998 A1 | 9/2019 | Seki |
| 2021/0182616 A1 | 6/2021 | Huang et al. |
| 2021/0192180 A1* | 6/2021 | Wang .................. G06V 20/698 |

FOREIGN PATENT DOCUMENTS

| | | |
|---|---|---|
| JP | 2018041176 | 3/2018 |
| JP | 2019153235 | 9/2019 |
| JP | 2019534520 | 11/2019 |
| JP | 2019207561 | 12/2019 |
| JP | 2020527812 | 9/2020 |
| WO | 2019015785 | 1/2019 |
| WO | 2019180414 | 9/2019 |

OTHER PUBLICATIONS

Hoel Kervadec; et al., "Constrained-CNN losses for weakly supervised segmentation," arXiv:1805.04628v2, Feb. 8, 2019, pp. 1-25.
"International Search Report (Form PCT/ISA/210) of PCT/JP2021/027590," mailed on Oct. 12, 2021, with English translation thereof, pp. 1-7.
"Written Opinion of the International Searching Authority (Form PCT/ISA/237) of PCT/JP2021/027590," mailed on Oct. 12, 2021, with English translation thereof, pp. 1-8.

* cited by examiner

COMPLETE INCLUSION RELATIONSHIP

PARTIAL INCLUSION RELATIONSHIP

INFORMATION PROCESSING APPARATUS, INFORMATION PROCESSING METHOD, AND NON-TRANSITORY COMPUTER-READABLE STORAGE MEDIUM FOR TRAINING AN ESTIMATION MODEL SUCH THAT A LOSS IS REDUCED

CROSS-REFERENCE TO RELATED APPLICATION

This application is a continuation application of International Application No. PCT/JP2021/027590, filed Jul. 26, 2021, the disclosure of which is incorporated herein by reference in its entirety. Further, this application claims priority from Japanese Patent Application No. 2020-163872 filed on Sep. 29, 2020, the disclosures of which is incorporated herein by reference in its entirety.

BACKGROUND

1. Technical Field

The disclosed technology relates to an information processing apparatus, an information processing method, and an information processing program.

2. Description of the Related Art

The following technologies are known as technologies related to segmentation for recognizing what an object included in an image is in a pixel unit.

For example, JP2017-532092A discloses a method implemented in a computer for segmenting a medical image. The method includes a step of receiving an image from a memory, a step of discriminating at least one landmark point in the image, a step of selecting an image point in the image, a step of deciding, by a processor, at least one feature for the image point relative to the at least one landmark point, and a step of associating, by the processor, the image point with an anatomical structure by using a classification model based on the decided at least one feature.

JP2018-041176A discloses a parking position specifying method in which at least one computer specifies a parking position of a target vehicle. The method includes acquiring input data which is an image generated by imaging a parking region with a camera mounted on the target vehicle, and specifying the parking position of the target vehicle in the imaged parking region by inputting the input data to a learning model showing a relationship between the parking region having an area in which at least one vehicle can be parked and the parking position of one vehicle in the parking region.

SUMMARY

Diagnostic imaging support is known as an example of utilization in a medical field of an image recognition technology using an estimation model trained by machine learning. For example, in rectal cancer, the cancer begins in a lumen of an intestinal tract and invades an outer tissue as the cancer progresses. Depending on whether or not the cancer has invaded peripheral tissues, the treatment policy or the region to be excised by surgery is changed. Therefore, in preoperative diagnosis, it is important to know an inclusion relationship between a cancer region and a peripheral tissue region. Specifying an inclusion relationship between the cancer region and the peripheral tissue region from the medical image, such as a magnetic resonance imaging (MRI) image and a computed tomography (CT) image, requires specialization and a heavy work load. Therefore, it is required to appropriately determine the presence or absence of cancer invasion into the peripheral tissues by using an estimation model, such as a neural network trained by machine learning, and to correctly visualize an invasion area in a case in which the invasion is observed.

In order to train the estimation model by machine learning, such as deep learning, it is necessary to prepare a large amount of training data in which area information indicating an area in which each of these regions is present is added as a correct answer mask to a training image including the cancer region and the peripheral tissue region. However, time and skill are required for the work of adding the area information (correct answer mask) to the training image. In addition, in a clinical image diagnosis process, although an image interpreter makes a determination for the presence or absence of the cancer invasion, it is usual that the area information is not created formally for each region. Therefore, it is not easy to prepare a large amount of training data in which area information is added to the training image.

The disclosed technology has been made in view of the above points, and is to train the estimation model such that the estimation model appropriately performs the segmentation for a plurality of regions included in an image which is a processing target, even in a case in which an amount of training data in which the area information is added to the training image is relatively small.

The disclosed technology relates to an information processing apparatus comprising at least one processor. A processor acquires a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images. The processor calculates, for each first training image, a first evaluation value for training an estimation model such that the plurality of regions specified by using the estimation model match the area information. The processor derives, for each second training image, estimation information in which the relationship indicated by the relationship information is estimated by using the estimation model to calculate a second evaluation value indicating a degree of deviation between the estimation information and the relationship information. The processor trains the estimation model such that a loss including, as elements, the first evaluation value and the second evaluation value is reduced.

The relationship between the plurality of regions may be an inclusion relationship between the plurality of regions. The plurality of training images may each include a first region and a second region including at least a part of the first region. The relationship information may be information indicating whether or not the first region has a portion that is not included in the second region in the second training image, and the estimation information may be a probability that the first region has the portion that is not included in the second region in the second training image. The processor may calculate, for each pixel of the second training image, a probability $P_x$ that the pixel is a pixel of the portion of the first region that is not included in the second region by using the estimation model, and may derive, as the estimation information, a value calculated based on the probability $P_x$ calculated for each pixel.

The training image may be a medical image, and the first region may be a lesion region and the second region may be a biological tissue region including at least a part of the lesion region.

The processor may acquire a target image including the first region and the second region, may specify at least one of the first region, the second region, or the portion of the first region that is not included in the second region by using the estimation model, and may perform control of displaying the specified region or portion in a discriminable manner.

The relationship between the plurality of regions may be a magnitude relationship between specific elements included respectively in the plurality of regions. The plurality of training images may each include a first region and a second region. The relationship information may be information indicating whether or not the element in the first region is larger than the element in the second region in the second training image, and the estimation information may be a probability that the element in the first region is larger than the element in the second region in the second training image. The processor may specify, for each second training image, the first region and the second region by using the estimation model, may derive a size $F_A$ of the element in the first region and a size $F_B$ of the element in the second region, and may derive, as the estimation information, a value according to a difference between the size $F_A$ of the element in the first region and the size $F_B$ of the element in the second region.

The relationship between the plurality of regions may be a positional relationship between the plurality of regions. The plurality of training images may each include a first region and a second region. The relationship information may be information indicating whether or not the first region is located in a specific direction with respect to the second region in the second training image, and the estimation information may be a probability that the first region is located in the specific direction with respect to the second region in the second training image.

The processor may calculate, for each pixel of the second training image, a probability $P_a$ that the pixel is the first region and a probability $P_b$ that the pixel is the second region by using the estimation model, may set a candidate region located in the specific direction with respect to a pixel at an end portion on a side in the specific direction among pixels in which the probability $P_b$ is equal to or larger than a threshold value, and may derive, as the estimation information, a value calculated based on the probability $P_a$ calculated for a pixel in the candidate region.

In a case in which the second evaluation value is E2, the estimation information is $y_k$, and the relationship information is $t_k$, the second evaluation value E2 may be determined such that Expression (I) is satisfied.

$$E2=\Sigma\{-t_K \log y_K-(1-t_K)\log(1-y_K)\} \quad (I)$$

The disclosed technology relates to an information processing method comprising acquiring a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images, calculating, for each first training image, a first evaluation value for training an estimation model such that the plurality of regions specified by using the estimation model match the area information, deriving, for each second training image, estimation information in which the relationship indicated by the relationship information is estimated by using the estimation model to calculate a second evaluation value indicating a degree of deviation between the estimation information and the relationship information, and training the estimation model such that a loss including, as elements, the first evaluation value and the second evaluation value is reduced.

The disclosed technology relates to an information processing program causing at least one processor provided in an information processing apparatus to execute a process comprising acquiring a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images, calculating, for each first training image, a first evaluation value for training an estimation model such that the plurality of regions specified by using the estimation model match the area information, deriving, for each second training image, estimation information in which the relationship indicated by the relationship information is estimated by using the estimation model to calculate a second evaluation value indicating a degree of deviation between the estimation information and the relationship information, and performing second learning processing of training the estimation model such that a loss including, as elements, the first evaluation value and the second evaluation value is reduced.

According to the disclosed technology, it is possible to train the estimation model such that the estimation model appropriately performs the segmentation for the plurality of regions included in the image which is the processing target, even in a case in which the amount of training data in which the area information is added to the training image is relatively small.

BRIEF DESCRIPTION OF THE DRAWINGS

Exemplary embodiments according to the technique of the present disclosure will be described in detail based on the following figures, wherein.

DETAILED DESCRIPTION

Figure 1:
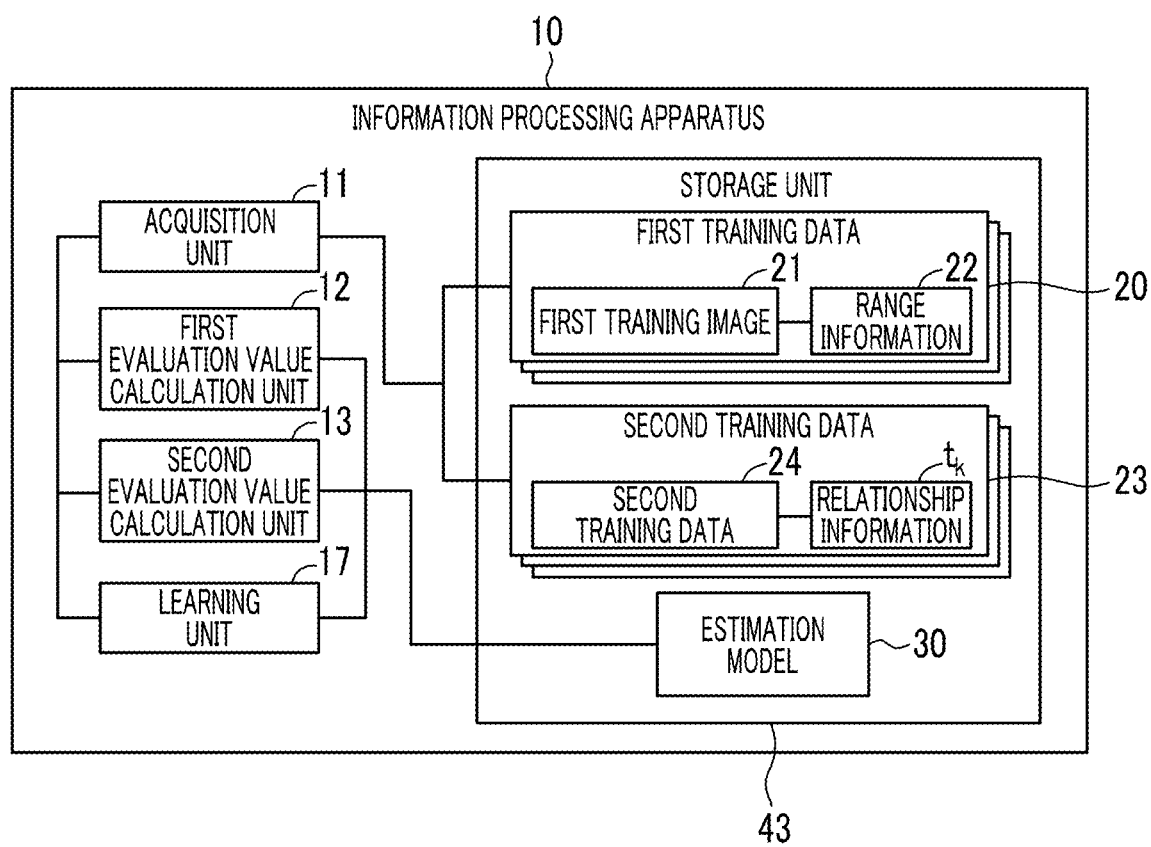
FIG. 1 is a diagram showing an example of a functional configuration of an information processing apparatus according to an embodiment of the disclosed technology in a learning phase.

Hereinafter, an example of embodiments of the disclosed technology will be described with reference to the drawings. It should be noted that the same or equivalent components and portions in the respective drawings are denoted by the same reference numerals, and the overlapping description will be omitted as appropriate.

First Embodiment

FIG. 1 is a diagram showing an example of a functional configuration of an information processing apparatus 10 according to the embodiment of the disclosed technology in a learning phase. The information processing apparatus 10 comprises an acquisition unit 11, a first evaluation value calculation unit 12, a second evaluation value calculation unit 13, a learning unit 17, and a storage unit 43. The storage unit 43 stores first training data 20, second training data 23, and an estimation model 30. In the learning phase, the information processing apparatus 10 performs processing of training the estimation model 30 by machine learning. The information processing apparatus 10 trains the estimation model 30 such that the estimation model 30 performs segmentation while specifying an inclusion relationship for a plurality of regions.

Figure 2A:
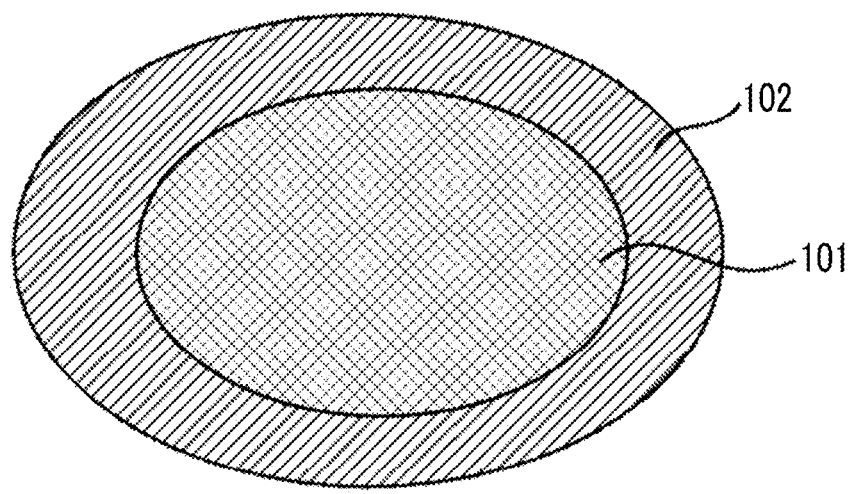
FIG. 2A is a diagram showing a case in which a plurality of regions have a complete inclusion relationship.
Figure 2B:
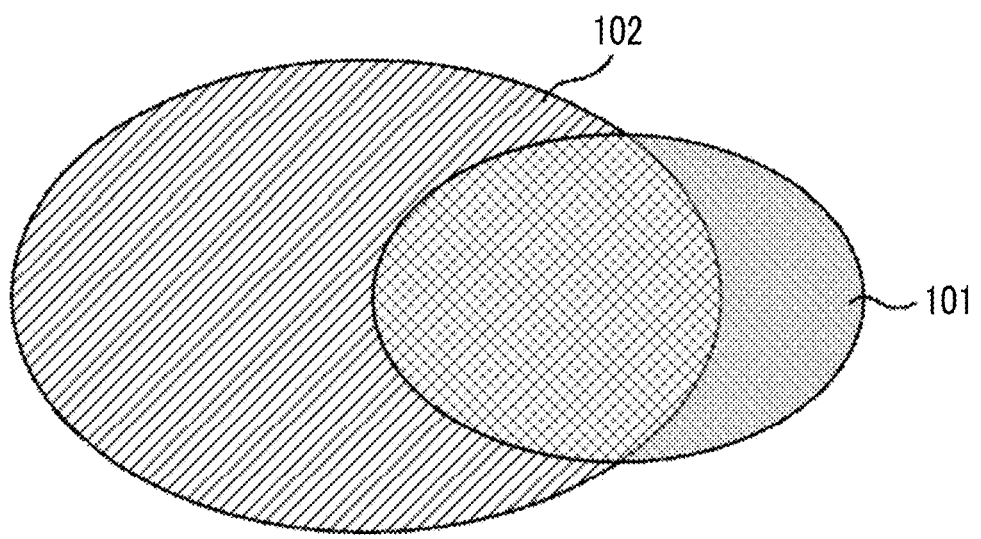
FIG. 2B is a diagram showing a case in which the plurality of regions have a partial inclusion relationship.

Here, FIG. 2A is a diagram showing an example of a state in which the inclusion relationship between a region 101 and a region 102 is a complete inclusion relationship. In the present specification, the term "complete inclusion relationship" refers to a relationship in which all portions of one region are included in the other region. FIG. 2B is a diagram showing an example of a state in which the inclusion relationship between the region 101 and the region 102 is a partial inclusion relationship. In the present specification, the term "partial inclusion relationship" refers to a relationship in which only a portion of one region is included in the other region. That is, in a case in which the two regions have the partial inclusion relationship, one region has a portion that is not included in the other region.

Figure 3A:
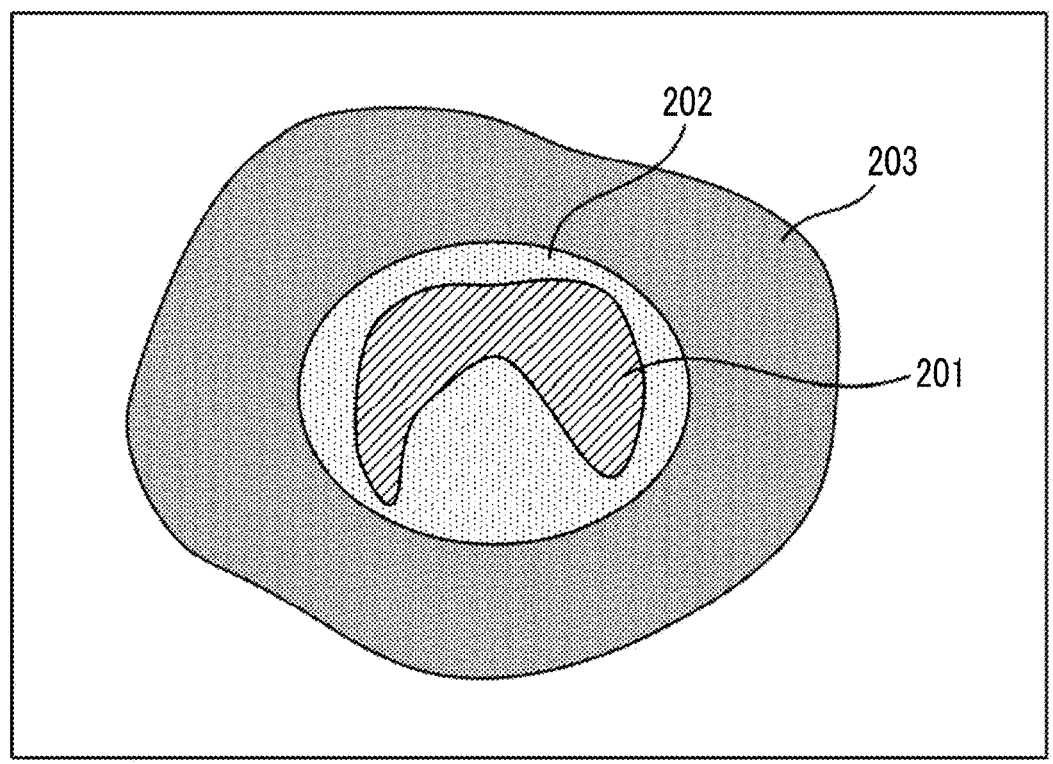
FIG. 3A is a tomographic image showing a case of rectal cancer.
Figure 3B:
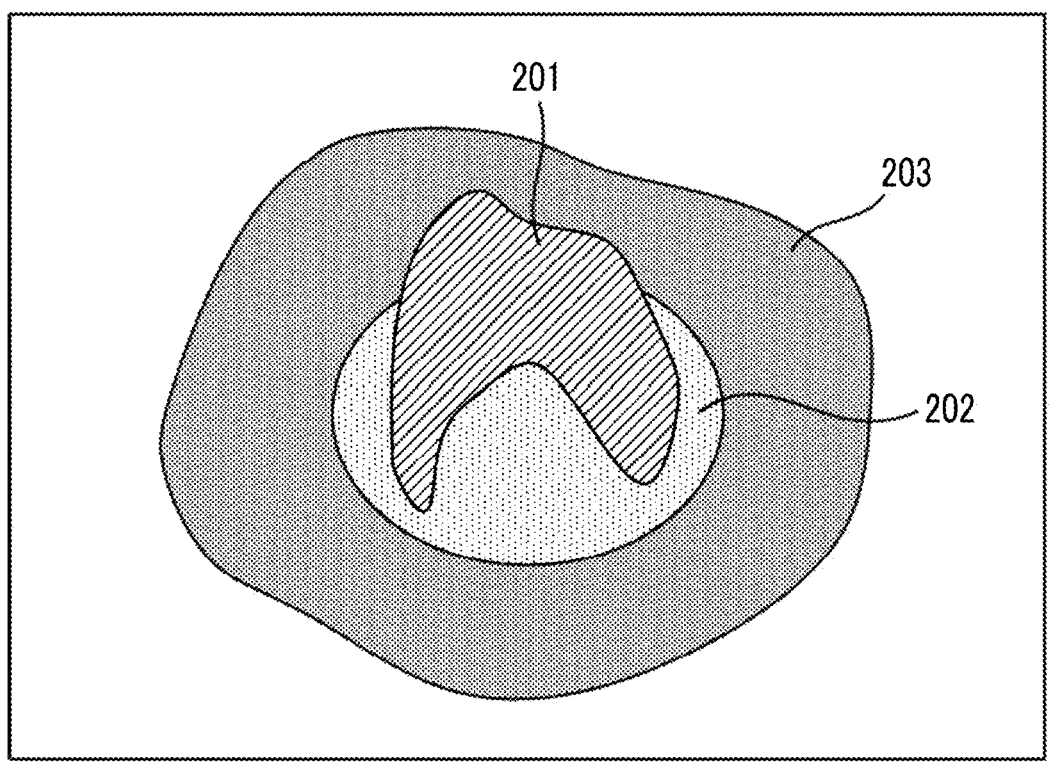
FIG. 3B is a tomographic image showing a case of the rectal cancer.

FIG. 3A and FIG. 3B are medical images (tomographic images) showing cases of rectal cancer, respectively. These tomographic images include a cancer region 201, a muscularis propria region 202, and a mesorectum region 203. FIG. 3A shows a case in which the cancer region 201 and the muscularis propria region 202 have the complete inclusion relationship, that is, a case of an early stage cancer in which the cancer region 201 has not invaded the mesorectum region 203. FIG. 3B shows a case in which the cancer region 201 and the muscularis propria region 202 have the partial inclusion relationship, that is, a case of advanced cancer in which the cancer region 201 has invaded the mesorectum region 203. In the following description, as an example, a case will be described in which the estimation model 30 performs the segmentation for the cancer region 201, the muscularis propria region 202, and the mesorectum region 203.

Figure 4:
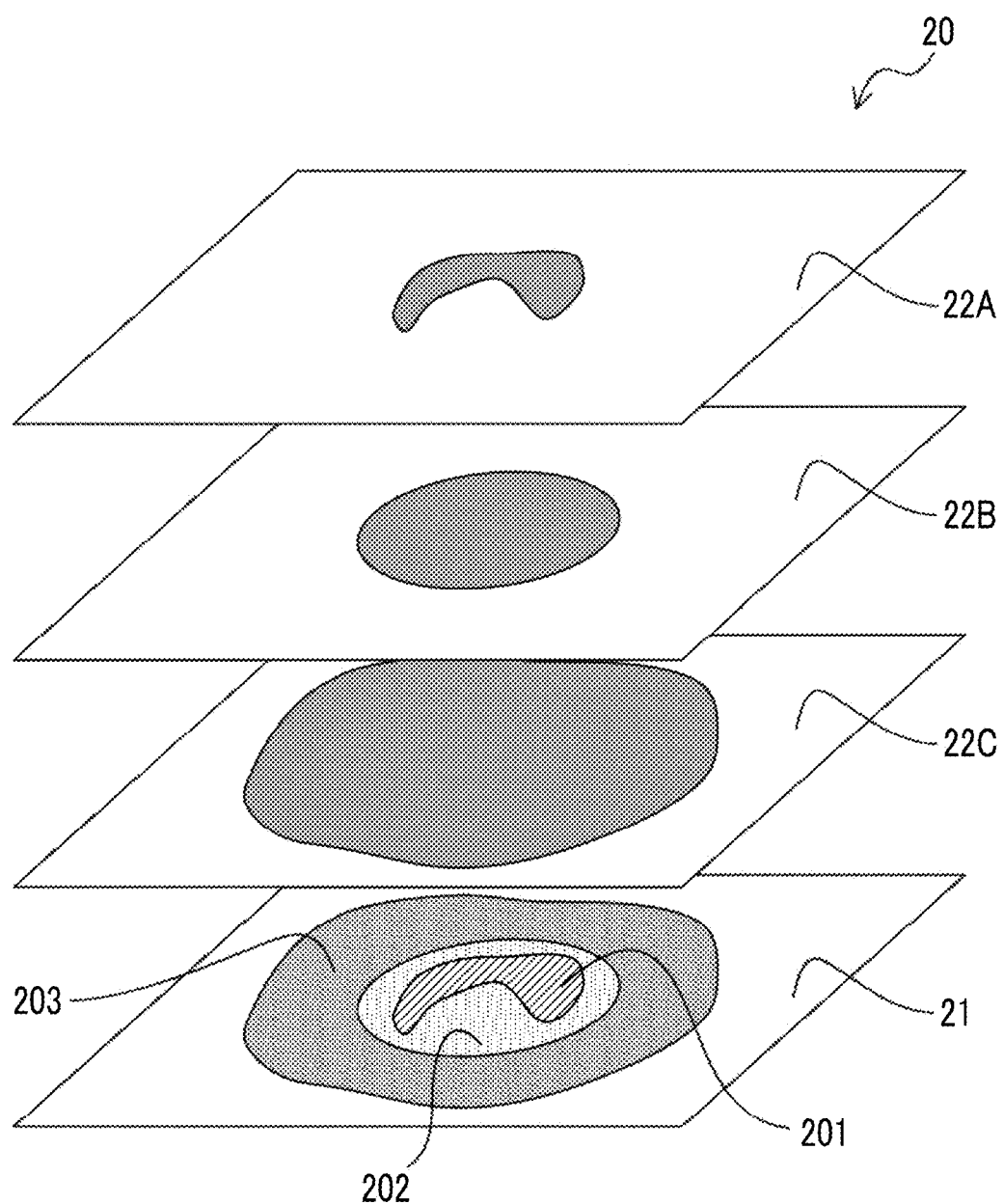
FIG. 4 is a diagram showing an example of first training data according to the embodiment of the disclosed technology.

The acquisition unit 11 acquires a plurality of first training data 20 and a plurality of second training data 23 stored in the storage unit 43. FIG. 4 is a diagram showing an example of the first training data 20. The first training data 20 is data in which area information 22 indicating an area in which each region is present is added as a correct answer mask to a first training image 21 including a plurality of regions. FIG. 4 shows a case in which the tomographic image showing the case of the rectal cancer, which is the medical image, is used as the first training image 21. The first training image 21 includes the cancer region 201, the muscularis propria region 202, and the mesorectum region 203. The cancer region 201 and the muscularis propria region 202 have the complete inclusion relationship or the partial inclusion relationship. It should be noted that the cancer region 201 is an example of a first region according to the disclosed technology, and the muscularis propria region 202 is an example of a second region according to the disclosed technology.

The first training data 20 is data in which area information 22A indicating an area in which the cancer region 201 is present, area information 22B indicating an area in which the muscularis propria region 202 is present, and area information 22C indicating an area in which the mesorectum region 203 is present are added as the correct answer masks to the first training image 21. In a case in which the inclusion relationship between the cancer region 201 and the muscularis propria region 202 included in the first training image 21 is the complete inclusion relationship, the entire area in which the cancer region is present indicated by the area information 22A is included in the area in which the muscularis propria region indicated by the area information 22B is present. On the other hand, in a case in which the inclusion relationship between the cancer region 201 and the muscularis propria region 202 included in the first training image 21 is the partial inclusion relationship, a part of the area in which the cancer region is present indicated by the area information 22A is not included in the area in which the muscularis propria region indicated by the area information 22B is present. In addition, in the first training image 21, both of these regions are assigned as correct answers to each pixel of a portion of the cancer region 201 that is included in the muscularis propria region 202.

It should be noted that it is preferable that the first training data 20 includes both the first training image 21 including a plurality of regions having the complete inclusion relationship and the first training image 21 including a plurality of regions having the partial inclusion relationship, but the first training data 20 may only include any one thereof.

The first evaluation value calculation unit 12 calculates a first evaluation value E1 for training the estimation model 30 using the plurality of first training data 20 acquired by the acquisition unit 11. The estimation model 30 is a mathematical model constructed to perform the segmentation on a pixel (voxel or pixel) unit for an image that is a processing target (hereinafter, referred to as a target image) including the plurality of regions. The estimation model 30 performs the segmentation on the plurality of regions included in the target image while specifying the inclusion relationship. That is, the estimation model 30 assigns the plurality of regions to the pixels of a portion in which a certain region is included in the other region. The estimation model 30 may constitute a neural network, for example.

The first evaluation value calculation unit 12 calculates, for each first training image 21, the first evaluation value E1 for training the estimation model 30 such that the cancer region 201, the muscularis propria region 202, and the mesorectum region 203 specified by using the estimation model 30 match the area information (correct answer masks) 22A, 22B, and 22C. The first evaluation value E1 may be a value indicating a degree of deviation between an estimation result of each region in the estimation model 30 and the area information 22A, 22B, and 22C. Expression (1) is an example of the first evaluation value E1. As shown in Expression (1), soft dice loss can be used as the first evaluation value E1. In Expression (1), $G_a$ is a correct answer value for each pixel based on the area information 22A, 1 is added to the pixel that is the cancer region 201, and 0 is added to the pixel that is not the cancer region 201. $P_a$ is a probability that the pixel is the cancer region 201, which is calculated by the estimation model 30. $G_b$ is a correct answer value for each pixel based on the area information 22B, 1 is added to the pixel that is the muscularis propria region 202, and 0 is added to the pixel that is not the muscularis propria region 202. $P_b$ is a probability that the pixel is the muscularis propria region 202, which is calculated by the estimation model 30. $G_c$ is a correct answer value for each pixel based on the area information 22C, 1 is added to the pixel that is the mesorectum region 203, and 0 is added to the pixel that is not the mesorectum region 203. $P_c$ is a probability that the pixel is the mesorectum region 203, which is calculated by the estimation model 30. $\gamma$, $\delta$, and $\varepsilon$ are weight constants for each class (cancer region 201, muscularis propria region 202, and mesorectum region 203), respectively. It should be noted that the first evaluation value E1 is not limited to soft dice loss indicated by Expression (1), other values can be used as long as a value indicates the degree of deviation between the estimation result of each region in the estimation model 30 and the area information 22. For example, the technologies described in U-Net: Convolutional Networks for Biomedical Image Segmentation arXiv:1505.04597 and Boundary loss for highly unbalanced segmentation arXiv:1812.07032 can be applied.

$$E1 = 1 - \frac{2}{\gamma + \delta + \varepsilon} \left( \frac{\sum(G_a * P_a)}{\sum G_a + \sum P_a} \times \gamma + \frac{\sum(G_b * P_b)}{\sum G_b + \sum P_b} \times \delta + \frac{\sum(G_c * P_c)}{\sum G_c + \sum P_c} \times \varepsilon \right) \quad (1)$$

Figure 5A:
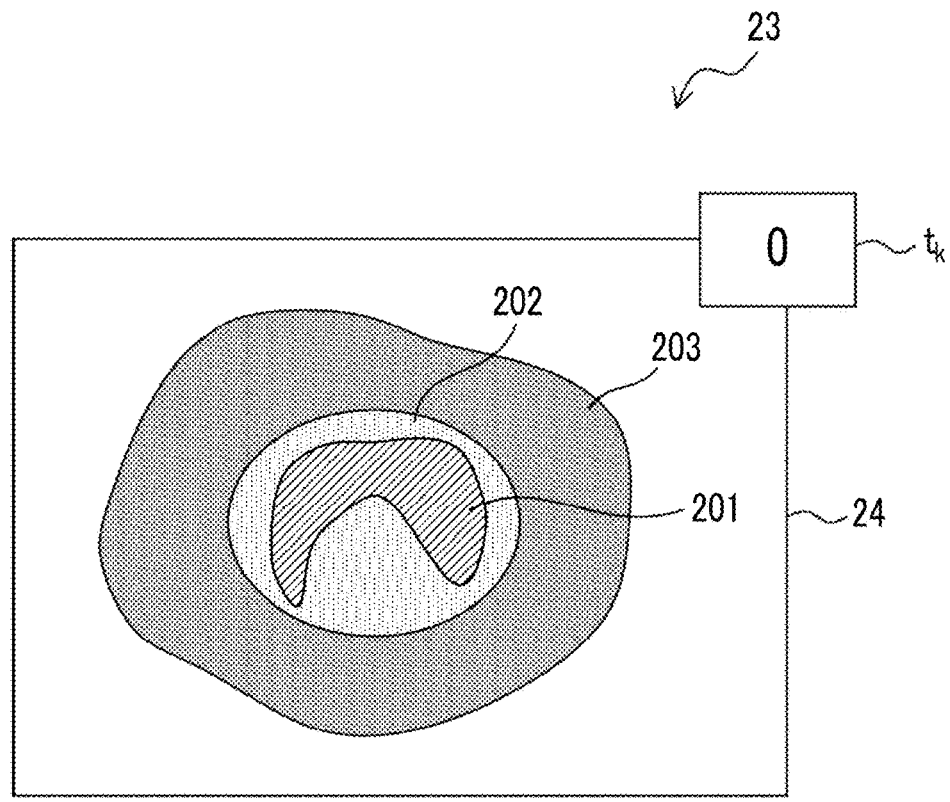
FIG. 5A is a diagram showing an example of second training data according to the embodiment of the disclosed technology.
Figure 5B:
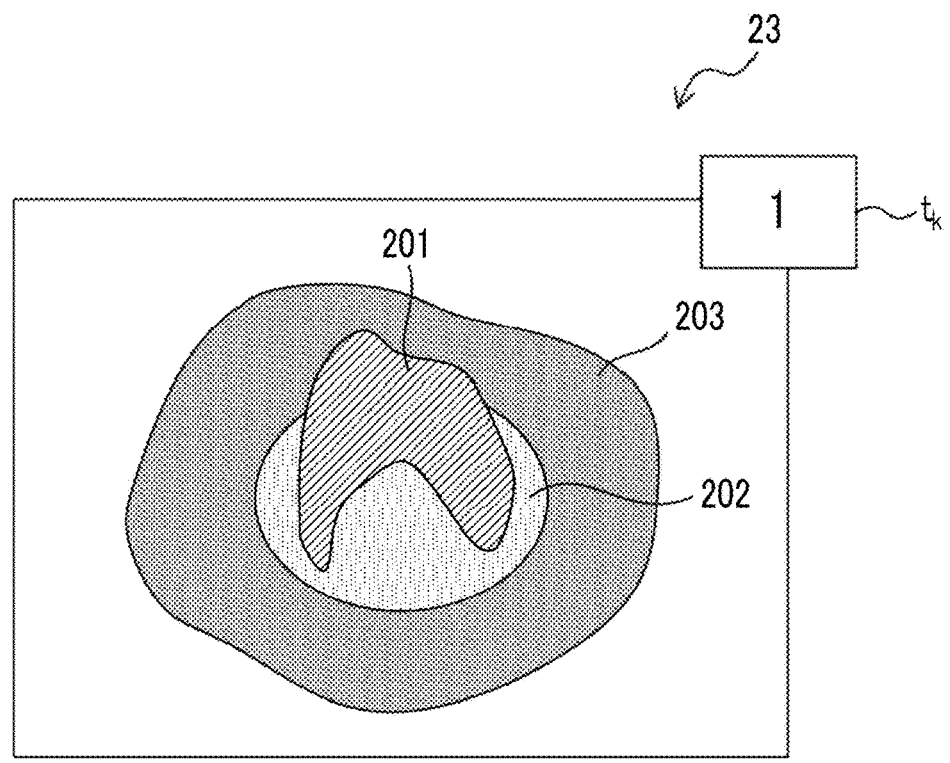
FIG. 5B is a diagram showing an example of the second training data according to the embodiment of the disclosed technology.

FIG. 5A and FIG. 5B are diagrams showing examples of the second training data 23, respectively. The second training data 23 is data in which relationship information $t_k$ indicating a relationship between a plurality of regions is added as a correct answer label to a second training image 24 including the plurality of regions. Similar to the first training image 21, FIG. 5A and FIG. 5B show a case in which the tomographic image showing the case of the rectal cancer, which is the medical image, is used as the second training image 24. Similar to the first training image 21, the second training image 24 includes the cancer region 201, the muscularis propria region 202, and the mesorectum region 203.

In the present embodiment, the relationship indicated by the relationship information $t_k$ is the inclusion relationship between the plurality of regions included in the second training image 24, and the relationship information $t_k$ is information indicating whether or not the cancer region 201 has a portion that is not included in the muscularis propria region 202 (that is, whether or not the cancer region 201 and the muscularis propria region 202 have the partial inclusion relationship) in the second training image 24. As shown in FIG. 5A, "0" is added as the relationship information $t_k$ to the second training image 24 in which the cancer region 201 does not have the portion that is not included in the muscularis propria region 202 (the cancer region 201 and the muscularis propria region 202 do not have the partial inclusion relationship). In other words, "0" is added as the relationship information $t_k$ to the second training image 24 of the case in which the cancer region 201 has not invaded the mesorectum region 203. On the other hand, as shown in FIG. 5B, "1" is added as the relationship information $t_k$ to the second training image 24 in which the cancer region 201 has the portion that is not included in the muscularis propria region 202 (the cancer region 201 and the muscularis propria region 202 have the partial inclusion relationship). In other words, "1" is added as the relationship information $t_k$ to the second training image 24 of the case in which the cancer region 201 has invaded the mesorectum region 203.

The second evaluation value calculation unit 13 calculates a second evaluation value E2 for training the estimation model 30 using the plurality of second training data 23 acquired by the acquisition unit 11. That is, in the training of the estimation model 30 using the second training data 23, the training is performed using the relationship indicated by the relationship information $t_k$ (in the present embodiment, the inclusion relationship between the cancer region 201 and the muscularis propria region 202) as a restriction condition.

In a case of calculating the second evaluation value E2, the second evaluation value calculation unit 13 derives, for each second training image, estimation information $y_k$ in which the relationship indicated by the relationship information $t_k$ is estimated by using the estimation model 30. That is, the second evaluation value calculation unit 13 derives, as the estimation information $y_k$, a result of estimation as to "whether or not the cancer region 201 has the portion that is not included in the muscularis propria region 202" in the second training image 24 by using the estimation model 30. Specifically, the second evaluation value calculation unit 13 derives, as the estimation information $y_k$, a probability that the cancer region 201 has the portion that is not included in the muscularis propria region 202 in the second training image 24. A method of deriving the estimation information $y_k$ is as follows.

The second evaluation value calculation unit 13 inputs the second training image 24 acquired by the acquisition unit 11 to the estimation model 30. The estimation model 30 performs the segmentation for each pixel on the input second training image 24. Specifically, the estimation model 30 calculates, for each pixel of the second training image 24, the probability $P_a$ that the pixel is the cancer region 201 and the probability $P_b$ that the pixel is the muscularis propria region 202. Further, the estimation model 30 calculates, for each pixel of the second training image 24, $P_a \times (1-P_b)$ as a probability $P_x$ in which the pixel is the portion of the cancer region 201 that is not included in the muscularis propria region 202 (portion of the cancer region that has invaded the mesorectum region). That is, the probability $P_x$ is calculated as the probability that the pixel is the cancer region 201 and is not the muscularis propria region 202. The estimation model 30 calculates the probabilities $P_a$, $P_b$, and $P_x$ for each pixel of each of a plurality of second training images 24.

The second evaluation value calculation unit 13 derives a value calculated based on the probability $P_x$ ($=P_a \times (1-P_b)$) calculated for each pixel of the second training image 24 as the estimation information $y_k$ (probability that the cancer region 201 has the portion that is not included in the muscularis propria region 202 in the second training image 24). The second evaluation value calculation unit 13 may calculate, for example, a maximum value of the probability $P_x$ calculated for each pixel of the second training image 24 as the estimation information $y_k$ in the second training image 24. In addition, the second evaluation value calculation unit 13 may calculate, for the probability $P_x$ calculated for each pixel of the second training image 24, an average value of some higher rank values in a case of ranking in descending order of the values as the estimation information $y_k$ in the second training image 24. In addition, the second evaluation value calculation unit 13 may calculate, for each pixel of the second training image 24, a probability $P_z$ ($=1-(P_a \times (1-P_b))$) that the pixel is not the portion of the cancer region that is not included in the muscularis propria region 202 to calculate a value $(1-\Pi P_z)$ obtained by subtracting the infinite product of the probability $P_z$ from 1 as the estimation information $y_k$. In addition to the above, an appropriate value as the probability that the cancer region 201 has the portion that is not included in the muscularis propria region 202 in the second training image 24 can be applied as the estimation information $y_k$.

The second evaluation value calculation unit 13 calculates the second evaluation value E2 indicating the degree of deviation between the estimation information $y_k$ and the relationship information $t_k$ as the correct answer label. The second evaluation value E2 is represented by Expression (2), for example.

$$E2 = \Sigma\{-t_K \log y_K - (1-t_K)\log(1-y_K)\} \quad (2)$$

That is, the second evaluation value E2 is a value obtained by integrating accumulating $-t_K \log y_K - (1-t_K) \log(1-y_K)$ calculated for each second training image 24 for all the second training images 24.

The learning unit 17 trains the estimation model 30 such that a loss L including the first evaluation value E1 and the second evaluation value E2 as elements is reduced. Expression (3) is an example of the loss L. In Expression (3), W1 is a weight constant with respect to the first evaluation value E1, and W2 is a weight constant with respect to the second evaluation value E2.

$$L = E1 \times W1 + E2 \times W2 \quad (3)$$

Figure 6:
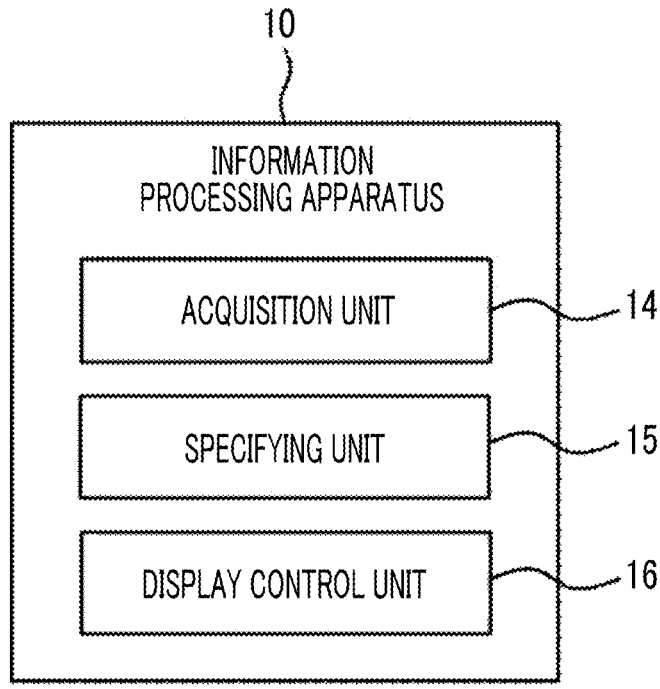
FIG. 6 is a diagram showing an example of a functional configuration of the information processing apparatus according to the embodiment of the disclosed technology in an operation phase.

FIG. 6 is a diagram showing an example of a functional configuration of the information processing apparatus 10 in an operation phase. In the operation phase, the information processing apparatus 10 operates the trained estimation model 30 to perform the segmentation for the plurality of regions included in the target image. The information processing apparatus 10 includes an acquisition unit 14, a specifying unit 15, and a display control unit 16.

The acquisition unit 14 acquires the target image including the plurality of regions that are the targets of the segmentation. Hereinafter, as an example, a case will be described in which the target image is the medical image similar to the first training image 21 shown in FIG. 4 and the second training image 24 shown in FIG. 5, the cancer region, the muscularis propria region, and the mesorectum region are included in the target image, and the segmentation is performed for each of these regions.

The specifying unit 15 inputs the target image acquired by the acquisition unit 14 to the trained estimation model 30. The estimation model 30 performs the segmentation for each pixel of the target image. Specifically, the estimation model 30 calculates, for each pixel of the target image, the probability $P_a$ that the pixel is the cancer region, the probability $P_b$ that the pixel is the muscularis propria region, and the probability $P_c$ that the pixel is the mesorectum region.

The specifying unit 15 specifies a region consisting of pixels in which the probability $P_a$ is equal to or larger than a predetermined threshold value as the cancer region, specifies a region consisting of pixels in which the probability $P_b$ is equal to or larger than the predetermined threshold value as the muscularis propria region, and specifies a region consisting of pixels in which the probability $P_c$ is equal to or larger than the threshold value as the mesorectum region. In addition, the specifying unit 15 specifies a region that is not the muscularis propria region among the regions specified as the cancer region as the portion of the cancer region that is not included in the muscularis propria region (portion of the cancer region that has invaded the mesorectum region).

Figure 7:
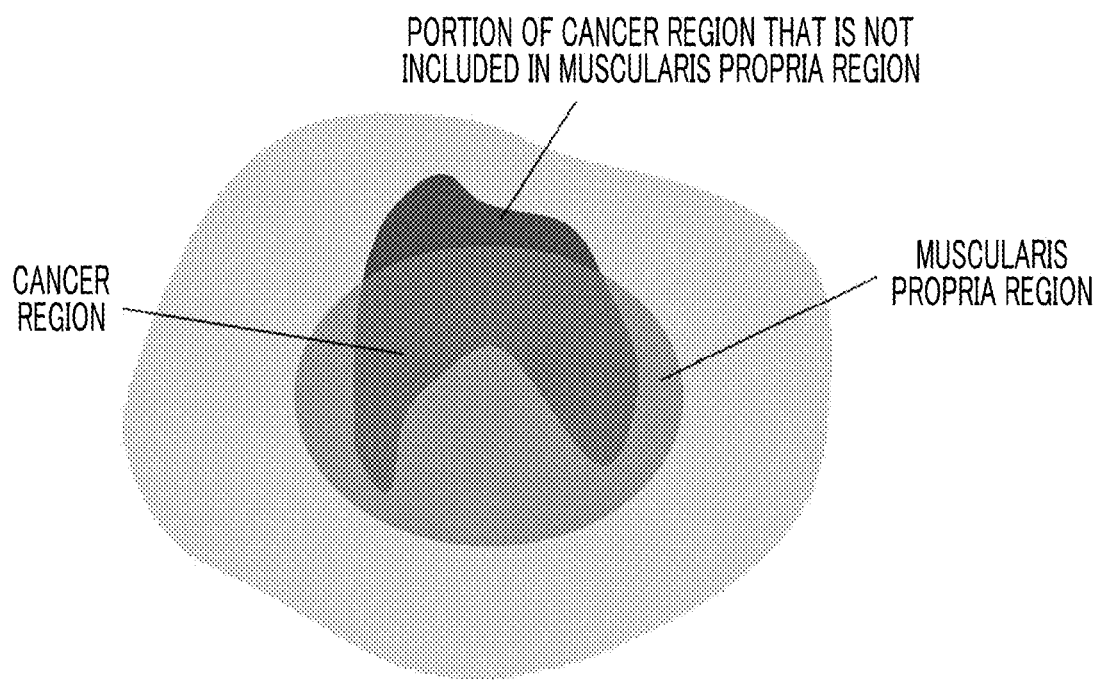
FIG. 7 is a diagram showing an example of display control in the information processing apparatus according to the embodiment of the disclosed technology.

The display control unit 16 performs control of displaying each region and portion specified by the specifying unit 15 in a discriminable manner. For example, as shown in FIG. 7, the display control unit 16 performs control of displaying color-coded label images indicating areas in which the cancer region, the muscularis propria region, and the portion of the cancer region that is not included in the muscularis propria region (portion of the cancer region that has invaded the mesorectum region) are present, respectively, in a manner of being superimposed on the target image. It should be noted that the specifying unit 15 may specify at least one of the cancer region, the muscularis propria region, or the portion that is not included in the muscularis propria region of the cancer region. In this case, the display control unit 16 performs control of displaying the region or portion specified by the specifying unit 15 in a discriminable manner.

Figure 8:
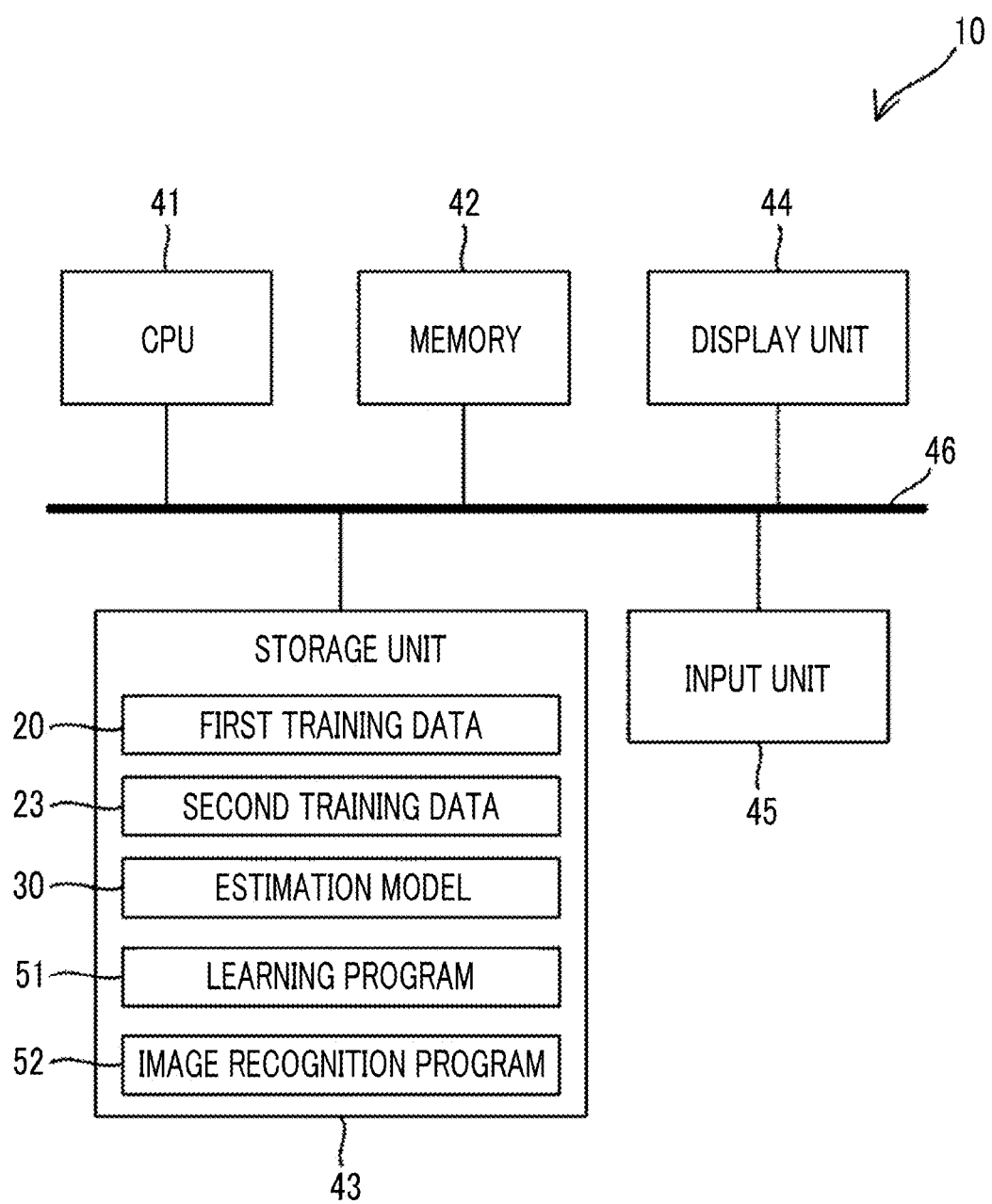
FIG. 8 is a diagram showing an example of a hardware configuration of the information processing apparatus according to the embodiment of the disclosed technology.

FIG. 8 is a diagram showing an example of a hardware configuration of the information processing apparatus 10. The information processing apparatus 10 comprises a central processing unit (CPU) 41, a memory 42 as a transitory storage area, and a non-volatile storage unit 43. In addition, the information processing apparatus 10 comprises a display unit 44 configured by a display device, such as a liquid crystal display, and an input unit 45 configured by an input device, such as a keyboard and a mouse. The CPU 41, the memory 42, the storage unit 43, the display unit 44, and the input unit 45 are connected to each other via a bus 46.

The storage unit 43 is realized by, for example, a non-volatile storage medium, such as a hard disk drive (HDD), a solid state drive (SSD), or a flash memory. The storage unit 43 stores the first training data 20, the second training data 23, the estimation model 30, a learning program 51, and an image recognition program 52. The CPU 41 loads the learning program 51 and the image recognition program 52 in the memory 42 and then executes the learning program 51 and the image recognition program 52. The CPU 41 executes the learning program 51, so that the CPU 41 functions as the acquisition unit 11, the first evaluation value calculation unit 12, the second evaluation value calculation unit 13, and the learning unit 17. In addition, the CPU 41 executes the image recognition program 52, so that the CPU 41 functions as the acquisition unit 14, the specifying unit 15, and the display control unit 16. The CPU 41 is an example of a processor according to the disclosed technology.

Figure 9:
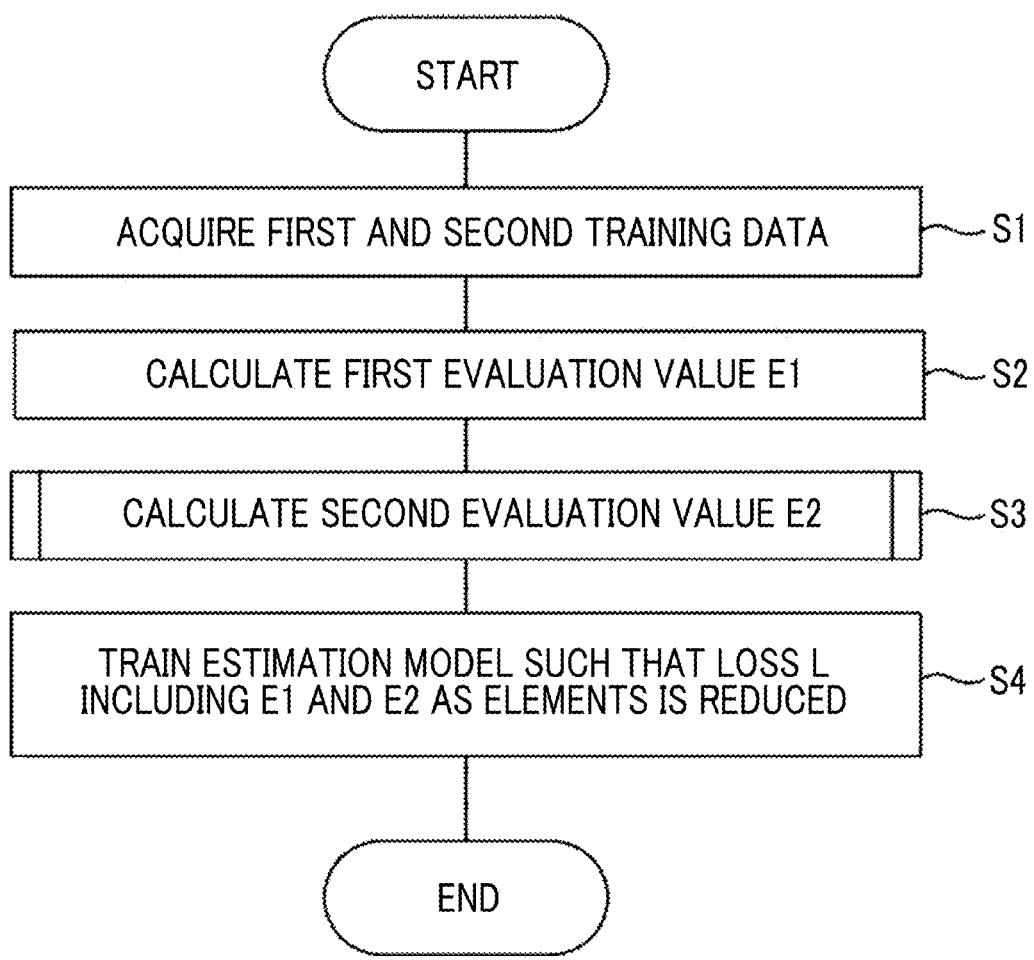
FIG. 9 is a flowchart showing an example of a flow of learning processing according to the embodiment of the disclosed technology.

FIG. 9 is a flowchart showing an example of a flow of learning processing executed by the CPU 41 executing the learning program 51. For example, the CPU 41 executes the learning program 51 in a case in which a user inputs an execution instruction of the learning processing via the input unit 45 in the learning phase.

In step S1, the acquisition unit 11 acquires the plurality of first training data 20 and the plurality of second training data 23 stored in the storage unit 43.

In step S2, the first evaluation value calculation unit 12 calculates the first evaluation value E1 for training the estimation model 30 using the first training data 20 acquired in step S1. More specifically, the first evaluation value calculation unit 12 calculates, for each first training image 21, the first evaluation value E1 for training the estimation model 30 such that the cancer region 201, the muscularis propria region 202, and the mesorectum region 203 specified by using the estimation model 30 match the area information 22A, 22B, and 22C. The first evaluation value E1 may be a value indicating the degree of deviation between the estimation result of each region in the estimation model 30 and the area information 22, and for example, the value represented by Expression (1) can be used.

Figure 10:
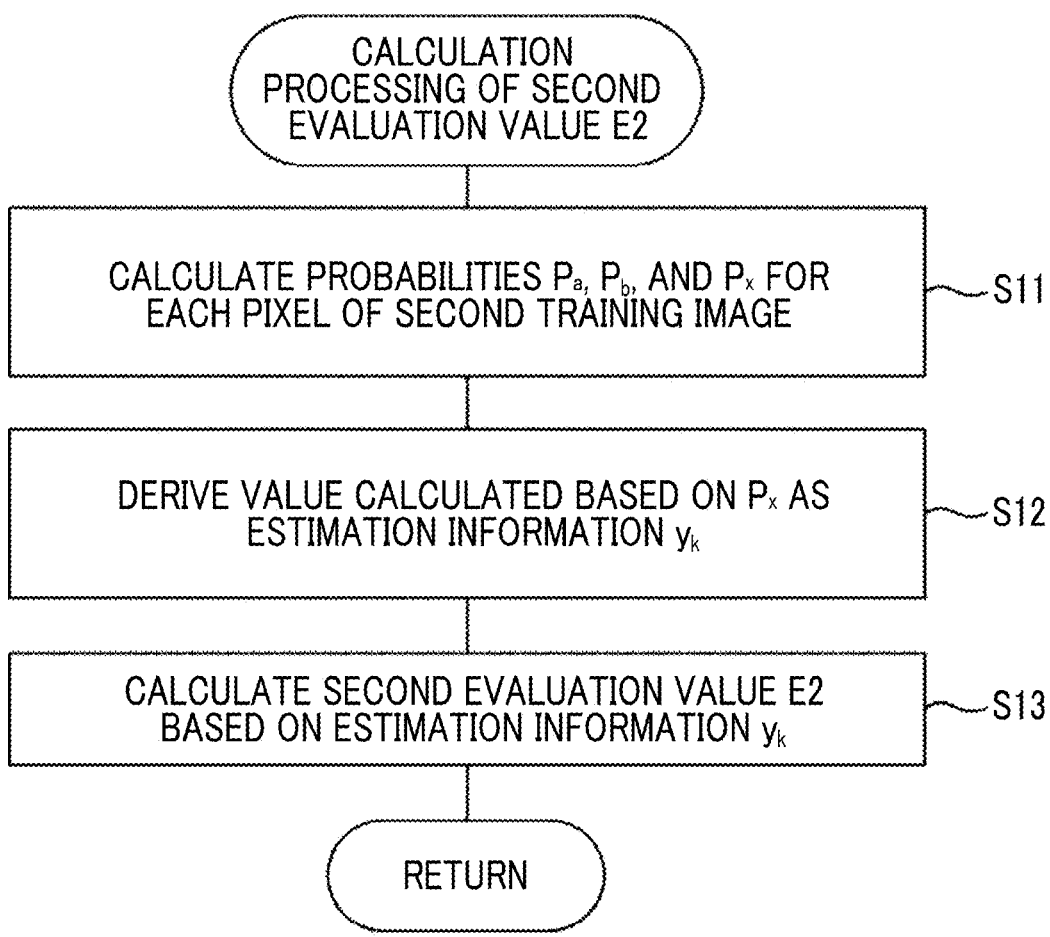
FIG. 10 is a flowchart showing an example of a flow of second learning processing according to the embodiment of the disclosed technology.

In step S3, the second evaluation value calculation unit 13 calculates the second evaluation value E2 for training the estimation model 30 using the second training data 23 acquired in step S1. FIG. 10 is a flowchart showing details of calculation processing of the second evaluation value E2. Hereinafter, the calculation processing of the second evaluation value E2 will be described with reference to FIG. 10.

In step S11, the second evaluation value calculation unit 13 calculates, for each pixel of each of the plurality of second training images 24, the probability $P_a$ that the pixel is the cancer region 201, the probability $P_b$ that the pixel is the muscularis propria region 202, and the probability $P_x$ ($=P_a \times (1-P_b)$) that the pixel is the portion of the cancer region 201 that is not included in the muscularis propria region 202 (portion of the cancer region that has invaded the mesorectum region) by using the estimation model 30.

In step S12, the second evaluation value calculation unit 13 derives a value calculated based on the probability $P_x$ calculated for each pixel of the second training image 24 as the estimation information $y_k$ of the second training image 24. As an example, the second evaluation value calculation unit 13 may derive the maximum value of the probability $P_x$ calculated for each pixel of the second training image 24 as the estimation information $y_k$ in the second training image 24. The second evaluation value calculation unit 13 derives the estimation information $y_k$ for each of the plurality of second training images 24.

In step S13, the second evaluation value calculation unit 13 calculates the second evaluation value E2 indicating the degree of deviation between the estimation information $y_k$ derived in step S12 and the relationship information $t_k$. As the second evaluation value E2, for example, a value represented by Expression (2) can be used.

In step S4 (see FIG. 9), the learning unit 17 trains the estimation model 30 such that the loss L including the first evaluation value E1 and the second evaluation value E2 as elements is reduced. As the loss L, for example, a value represented by Expression (3) can be used. The estimation model 30 is optimized by repeatedly executing the processing of steps S1 to S4 while exchanging the data sets of the first training data 20 and the second training data 23 to be used.

Figure 11:
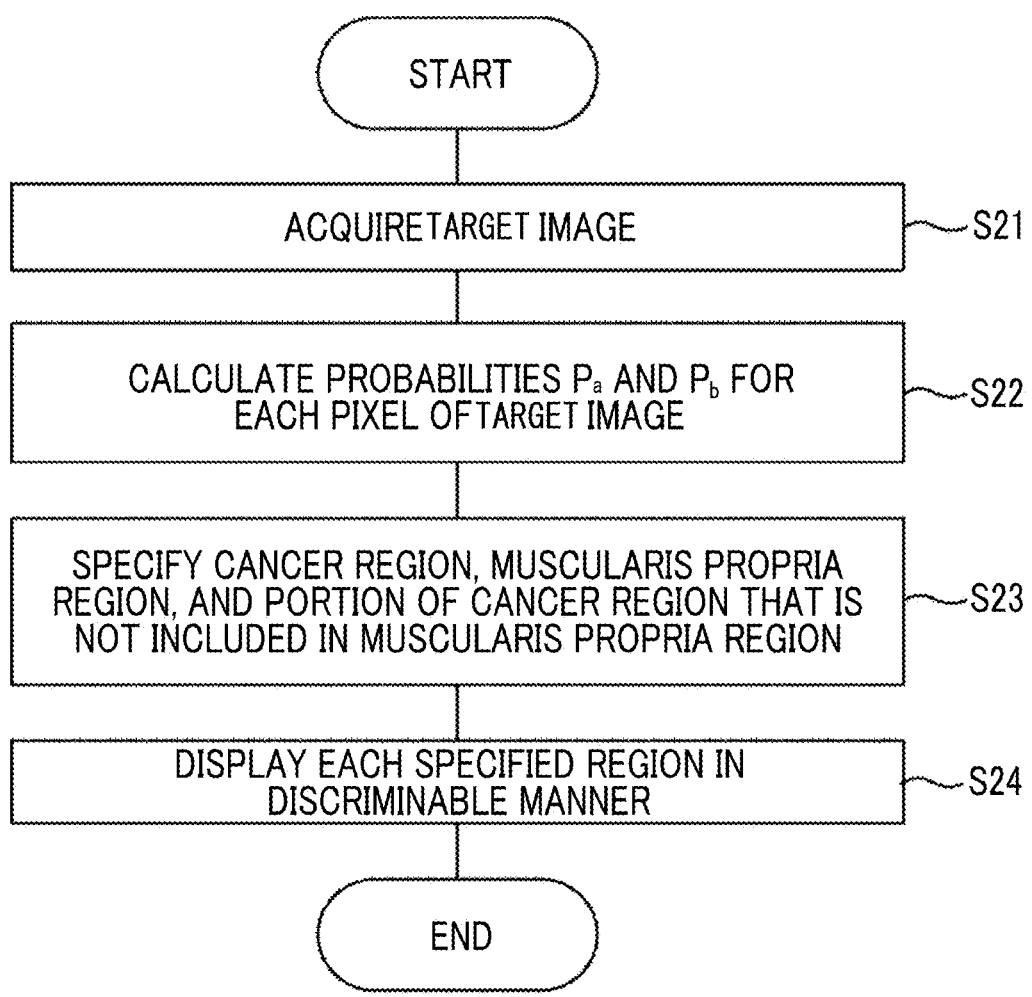
FIG. 11 is a flowchart showing an example of a flow of image recognition processing according to the embodiment of the disclosed technology.

FIG. 11 is a flowchart showing an example of a flow of image recognition processing executed by the CPU 41 executing the image recognition program 52. For example, the CPU 41 executes the image recognition program 52 in a case in which the user inputs an execution instruction of the image recognition processing via the input unit 45 in the operation phase.

In step S21, the acquisition unit 14 acquires the target image including the cancer region, the muscularis propria region, and the mesorectum region. In step S22, the specifying unit 15 calculates, for each pixel of the target image, the probability $P_a$ that the pixel is the cancer region and the probability $P_b$ that the pixel is the muscularis propria region by using the trained estimation model 30.

In step S23, the specifying unit 15 specifies the region consisting of pixels in which the probability $P_a$ is equal to or larger than the predetermined threshold value as the cancer region, and specifies the region consisting of pixels in which the probability $P_b$ is equal to or larger than the predetermined threshold value as the muscularis propria region. In addition, the specifying unit 15 specifies a region that is not the muscularis propria region among the regions specified as the cancer region as the portion of the cancer region that is not included in the muscularis propria region (portion of the cancer region that has invaded the mesorectum region).

In step S24, the display control unit 16 performs control of displaying each region and portion specified in step S23 in a discriminable manner. As shown in FIG. 7, the display control unit 16 performs, on the display unit 44, control of displaying the color-coded label images indicating areas in which the cancer region, the muscularis propria region, and the portion of the cancer region that is not included in the muscularis propria region (portion of the cancer region that has invaded the mesorectum region) are present, respectively, in a manner of being superimposed on the target image.

As described above, in the learning phase in which the estimation model 30 is trained, the information processing apparatus 10 according to the embodiment of the disclosed technology acquires the plurality of first training data 20 in which the area information 22 (22A, 22B, and 22C) indicating the area in which each of the plurality of regions is present is added to the first training image 21 that is at least a part of the plurality of training images each including the plurality of regions (cancer region 201, muscularis propria region 202, and mesorectum region 203). The information processing apparatus 10 acquires the plurality of second training data 23 in which the relationship information $t_k$ indicating the relationship between the plurality of regions is added to the second training image 24 that is at least a part of the plurality of training images. The information processing apparatus 10 calculates, for each first training image 21, the first evaluation value E1 for training the estimation model 30 such that the plurality of regions specified by using the estimation model 30 match the area information 22 (22A, 22B, and 22C). The information processing apparatus 10 derives, for each second training image 24, the estimation information $y_k$ in which the relationship indicated by the relationship information $t_k$ is estimated by using the estimation model 30. The information processing apparatus 10 calculates the second evaluation value E2 indicating the degree of deviation between the estimation information $y_k$ and the relationship information $t_k$. The information processing apparatus 10 trains the estimation model 30 such that the loss L including the first evaluation value E1 and the second evaluation value E as elements is reduced.

In general, in order to train the estimation model that performs the segmentation on the plurality of regions included in the target image, it is necessary to prepare a large amount of training data (first training data according to the present embodiment) in which the area information indicating the area in which each of these regions is present is added as the correct answer mask to the training image including the plurality of regions which are targets of the segmentation. However, since time and skill are required for the work of adding the area information to the training image, it is not easy to prepare a large amount of such training data.

The information processing apparatus 10 according to the embodiment of the disclosed technology trains the estimation model 30 using the second training data 23 in which the relationship information $t_k$ is added as the correct answer label to the second training image 24, in addition to the first training data 20 in which the area information 22 (22A, 22B, and 22C) is added as the correct answer mask to the first training image 21. Therefore, even in a case in which the amount of the first training data 20 is relatively small, since the complementation is performed by the second training data 23, the estimation model 30 can be appropriately trained. The relationship information $t_k$ is the information indicating whether or not the plurality of regions included in the second training image 24 have a predetermined relationship, and the acquisition and the addition to the training image are easier than the area information 22 (22A, 22B, and 22C). That is, it is relatively easy to prepare a necessary and sufficient amount of the second training data 23 for training the estimation model 30.

In addition, with the information processing apparatus 10 according to the embodiment of the disclosed technology, the estimation model 30 is trained using the second training data 23 with the inclusion relationship between the plurality of regions, which are targets of the segmentation, as the restriction condition, it is possible to improve the specificity (probability of correctly determining a case not having the partial inclusion relationship as being not having the partial inclusion relationship) as compared with a case in which the estimation model 30 is trained using only the first training data 20.

In addition, in the operation phase in which the trained estimation model 30 is operated, the information processing apparatus 10 according to the embodiment of the disclosed technology acquires the target image including the first region and the second region, specifies at least one of the first region, the second region, or the portion of the first region that is not included in the second region by using the estimation model 30, and performs control of displaying the specified region or portion in a discriminable manner. With the information processing apparatus 10, it is possible to visualize, for example, the presence or absence of invasion of the cancer region into the peripheral tissues and the invasion area.

It should be noted that, in the above description, the case has been described in which the segmentation is performed on the cancer region and the muscularis propria region included in the medical image, but the disclosed technology can also be applied to a case in which the segmentation is performed on the lesion region other than the cancer region and the biological tissue region other than the muscularis propria region. In addition, the case has been described in which the target image is the medical image, but the disclosed technology is not limited to this. For example, the disclosed technology can also be applied to a case in which the segmentation is performed on a plurality of regions included in a microscopic image, an inspection image used in an inspection step of a production line, or the like.

In addition, in the above description, the case has been described in which the training data in which any one of the area information 22 or the relationship information $t_k$ is added to the training image is used, but the training data in which both the area information 22 and the relationship information $t_k$ are added to the training image can also be used. In this case, one of the first training data 20 or the second training data 23 can also serve as the other.

Second Embodiment

In the first embodiment, the case has been described in which the relationship indicated by the relationship information $t_k$ is the inclusion relationship between the plurality of regions included in the second training image 24, and the relationship information $t_k$ is the information indicating whether or not the cancer region 201 has the portion that is not included in the muscularis propria region 202 in the second training image 24. In the second embodiment, the relationship indicated by the relationship information $t_k$ is a magnitude relationship between specific elements included respectively in the plurality of regions (first region and second region) included in the second training image 24, and the relationship information $t_k$ is information indicating whether or not the specific element in the first region is larger than the specific element in the second region. The specific element is not particularly limited as long as an element can be recognized from the second training image 24, and examples thereof include a volume, a brightness, and a surface area per volume.

In the second training data 23, "0" is added as the relationship information $t_k$ to the second training image 24 in which the specific element in the first region is smaller than the specific element in the second region. On the other hand, in the second training data 23, "1" is added as the relationship information $t_k$ to the second training image 24 in which the specific element in the first region is larger than the specific element in the second region.

The second evaluation value calculation unit 13 calculates the second evaluation value E2 for training the estimation model 30 using the plurality of second training data 23 acquired by the acquisition unit 11. In the training using the second training data 23 according to the present embodiment, the training is performed using the magnitude relationship between specific elements included respectively in the first region and the second region as the restriction condition. Hereinafter, the calculation processing of the second evaluation value E2 according to the present embodiment will be described in detail.

In a case of calculating the second evaluation value E2, the second evaluation value calculation unit 13 derives, for each second training image 24, the estimation information $y_k$ in which the relationship indicated by the relationship information $t_k$ is estimated by using the estimation model 30. That is, the second evaluation value calculation unit 13 derives, as the estimation information $y_k$, a result of estimation as to "whether or not the specific element in the first region is larger than the specific element in the second region" in the second training image 24 by using the estimation model 30. Specifically, the second evaluation value calculation unit 13 derives the probability that the specific element in the first region is larger than the specific element in the second region in the second training image 24 as the estimation information $y_k$. Hereinafter, a method of deriving the estimation information $y_k$ will be described.

The second evaluation value calculation unit 13 inputs the second training image 24 acquired by the acquisition unit 11 to the estimation model 30. The estimation model 30 performs the segmentation for each pixel on the input second training image 24 to specify the first region and the second region. For example, by using the estimation model 30, for each pixel of the second training image 24, the probability $P_a$ in which the pixel is in the first region and the probability $P_b$ in which the pixel is in the second region may be calculated, the region consisting of pixels in which the probability $P_a$ is equal to or larger than the threshold value may be specified as the first region, and the region consisting of pixels in which the probability $P_b$ is equal to or larger than the threshold value may be specified as the second region.

The second evaluation value calculation unit 13 derives a size $F_A$ of the specific element in the specified first region and a size $F_B$ of the specific element in the specified second region. $F_A$ and $F_B$ can be derived by analyzing the second training image 24.

The second evaluation value calculation unit 13 derives, for each second training images 24, a value according to a difference between $F_A$ and $F_B$ as the estimation information $y_k$ (probability that the specific element in the first region is larger than the specific element in the second region). For example, the second evaluation value calculation unit 13 may derive sigmoid $\{(F_A-F_B)/(F_A+F_B)\}$ as the estimation information $y_k$. It should be noted that sigmoid $(x)=1/(1+e^{-x})$.

The second evaluation value calculation unit 13 calculates the second evaluation value E2 indicating the degree of deviation between the estimation information $y_k$ and the relationship information $t_k$ derived as described above as the correct answer label. As the second evaluation value E2, for example, the value represented by Expression (2) can be used. The learning unit 17 trains the estimation model 30 such that the loss L including the first evaluation value E1 and the second evaluation value E2 as elements is reduced. It should be noted that the first evaluation value E1 can be calculated in the same manner as in the first embodiment.

Figure 12:
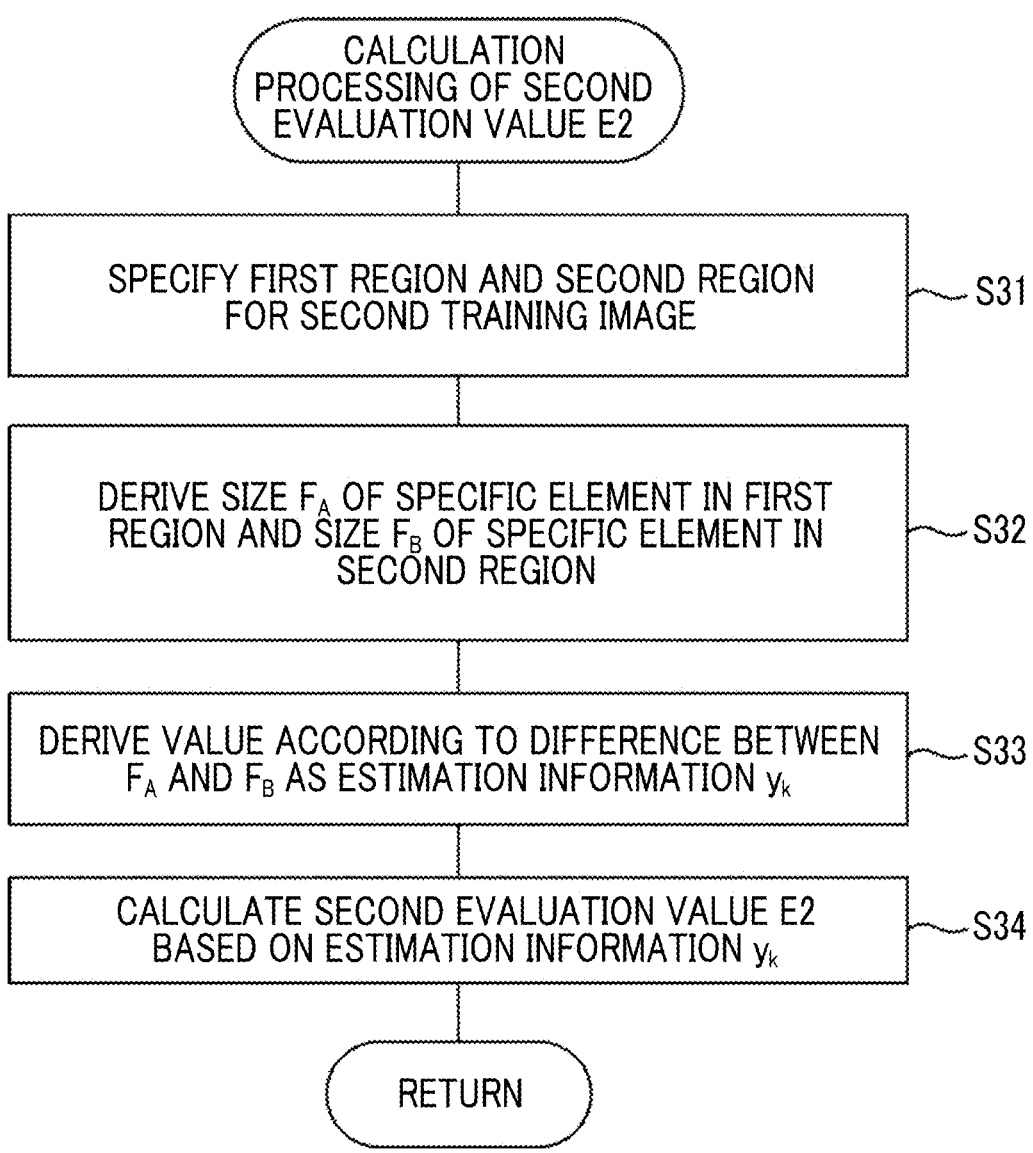
FIG. 12 is a flowchart showing an example of a flow of second learning processing according to another embodiment of the disclosed technology.

FIG. 12 is a flowchart showing details of the calculation processing of the second evaluation value E2 according to the second embodiment. Hereinafter, the calculation processing of the second evaluation value E2 according to the second embodiment will be described with reference to FIG. 12.

In step S31, the second evaluation value calculation unit 13 specifies the first region and the second region for each second training image by using the estimation model 30.

In step S32, the second evaluation value calculation unit 13 derives, for each second training image, the size $F_A$ of the specific element in the first region and the size $F_B$ of the specific element in the second region.

In step S33, the second evaluation value calculation unit 13 derives, for each second training image, the sigmoid $\{(F_A-F_B)/(F_A+F_B)\}$ as the estimation information $y_k$.

In step S34, the second evaluation value calculation unit 13 calculates the second evaluation value E2 indicating the degree of deviation between the estimation information $y_k$ derived in step S33 and the relationship information $t_k$. As the second evaluation value E2, for example, the value represented by Expression (2) can be used.

With the information processing apparatus 10 according to the present embodiment, as in the first embodiment, even in a case in which the amount of the first training data 20 is relatively small, since the complementation is performed by the second training data 23, the estimation model 30 can be appropriately trained.

Third Embodiment

In the first embodiment, the case has been described in which the relationship indicated by the relationship information $t_k$ is the inclusion relationship between the plurality of regions included in the second training image 24, and the relationship information $t_k$ is the information indicating whether or not the cancer region 201 has the portion that is not included in the muscularis propria region 202 in the second training image 24. In the third embodiment, the relationship indicated by the relationship information $t_k$ is a positional relationship between the plurality of regions (first region and second region) included in the second training image 24, and the relationship information $t_k$ is information indicating whether or not the first region is located in a specific direction with respect to the second region in the second training image 24. The specific direction is, for example, up, down, left, and right directions. In the following description, as an example, a case will be described in which the specific direction is the right direction.

In the second training data 23, "1" is added as the relationship information $t_k$ to the second training image 24 in which the first region is located in the right direction with respect to the second region. On the other hand, in the second training data 23, "0" is added as the relationship information $t_k$ to the second training image 24 in which the first region is not located in the right direction with respect to the second region.

The second evaluation value calculation unit 13 calculates the second evaluation value E2 for training the estimation model 30 using the plurality of second training data 23 acquired by the acquisition unit 11. In the training using the second training data 23 according to the present embodiment, the training is performed using the positional relationship between the first region and the second region as the restriction condition. Hereinafter, the calculation processing of the second evaluation value E2 according to the present embodiment will be described in detail.

In a case of calculating the second evaluation value E2, the second evaluation value calculation unit 13 derives, for each second training image 24, the estimation information $y_k$ in which the relationship indicated by the relationship information $t_k$ is estimated by using the estimation model 30. That is, the second evaluation value calculation unit 13 derives, as the estimation information $y_k$, a result of estimation as to "whether or not the first region is located in the right direction with respect to the second region" in the second training image 24 by using the estimation model 30. Specifically, the second evaluation value calculation unit 13 derives, as the estimation information $y_k$, a probability that the first region is located in the right direction with respect to the second region in the second training image 24. Hereinafter, the method of deriving the estimation information $y_k$ will be described.

The second evaluation value calculation unit 13 inputs the second training image 24 acquired by the acquisition unit 11 to the estimation model 30. The estimation model 30 performs the segmentation for each pixel on the input second training image 24. Specifically, the estimation model 30 calculates, for each pixel of the second training image 24, the probability $P_a$ in which the pixel is the first region and the probability $P_b$ in which the pixel is the second region.

The second evaluation value calculation unit 13 sets, as a candidate region, a region located on a right side with respect to the pixel at a right end portion among the pixels in which the probability $P_b$ is equal to or larger than the threshold value. The second evaluation value calculation unit 13 derives a value calculated based on the probability $P_a$ calculated for each pixel in the set candidate region as the estimation information $y_k$ (probability that the first region is located in the right direction with respect to the second region) in the second training image 24. The second evaluation value calculation unit 13 may derive, for example, a maximum value of the probability $P_a$ calculated for each pixel in the candidate region as the estimation information $y_k$ in the second training image 24.

The second evaluation value calculation unit 13 calculates the second evaluation value E2 indicating the degree of deviation between the estimation information $y_k$ and the relationship information $t_k$ derived as described above as the correct answer label. As the second evaluation value E2, for example, the value represented by Expression (2) can be used. The learning unit 17 trains the estimation model 30 such that the loss L including the first evaluation value E1 and the second evaluation value E2 as elements is reduced. It should be noted that the first evaluation value E1 can be calculated in the same manner as in the first embodiment.

Figure 13:
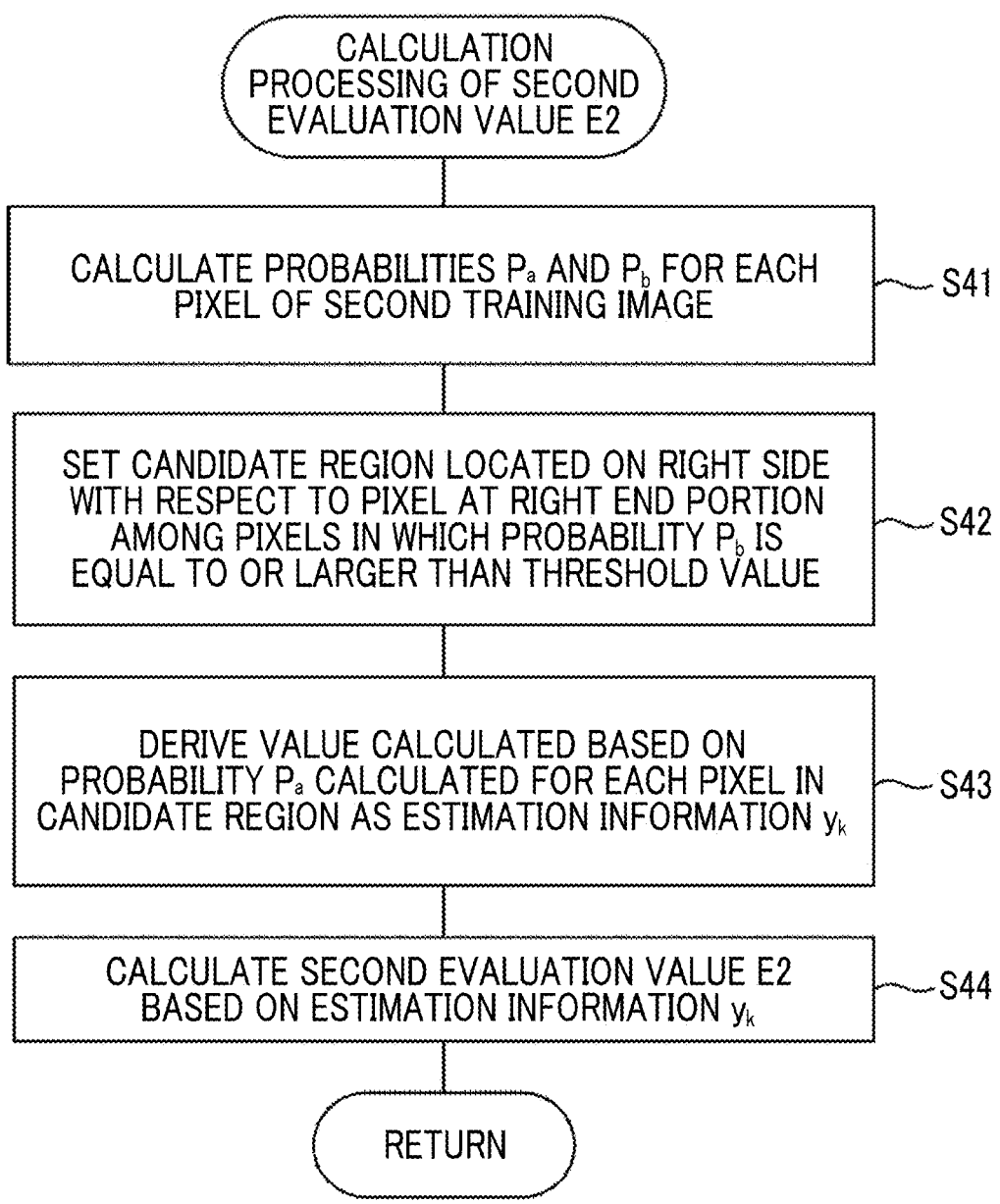
FIG. 13 is a flowchart showing an example of a flow of second learning processing according to still another embodiment of the disclosed technology.

FIG. 13 is a flowchart showing details of the calculation processing of the second evaluation value E2 according to the third embodiment. Hereinafter, the calculation processing of the second evaluation value E2 according to the third embodiment will be described with reference to FIG. 13.

In step S41, the second evaluation value calculation unit 13 calculates, for each pixel of each second training image 24, the probability $P_a$ that the pixel is the first region and the probability $P_b$ that the pixel is the second region by using the estimation model 30.

In step S42, the second evaluation value calculation unit 13 sets, for each second training image 24, the candidate region located on the right side with respect to the pixel at the right end portion among the pixels in which the probability $P_b$ is equal to or larger than the threshold value.

In step S43, the second evaluation value calculation unit 13 derives, for each second training image, a value calculated based on the probability $P_a$ calculated for each pixel in the candidate region as the estimation information $y_k$. The second evaluation value calculation unit 13 may derive, for example, the maximum value of the probability $P_a$ calculated for each pixel in the candidate region as the estimation information $y_k$ in the second training image 24.

In step S44, the second evaluation value calculation unit 13 calculates the second evaluation value E2 indicating the degree of deviation between the estimation information $y_k$ derived in step S43 and the relationship information $t_k$. As the second evaluation value E2, for example, the value represented by Expression (2) can be used.

With the information processing apparatus 10 according to the present embodiment, as in the first embodiment, even in a case in which the amount of the first training data 20 is relatively small, since the complementation is performed by the second training data 23, the estimation model 30 can be appropriately trained.

In addition, in each embodiment described above, various processors shown below can be used as the hardware structure of processing units that execute various types of processing, such as the acquisition unit 11, the first evaluation value calculation unit 12, the second evaluation value calculation unit 13, the learning unit 17, the acquisition unit 14, the specifying unit 15, and the display control unit 16. The various processors include, as described above, in addition to the CPU, which is a general-purpose processor which executes software (program) and functions as various processing units, a programmable logic device (PLD) which is a processor whose circuit configuration can be changed after manufacture, such as an FPGA, and a dedicated electric circuit which is a processor having a circuit configuration which is designed for exclusive use in order to execute specific processing, such as an application specific integrated circuit (ASIC).

One processing unit may be configured by one of the various processors or may be configured by a combination of two or more processors of the same type or different types (for example, a combination of a plurality of FPGAs or a combination of a CPU and an FPGA). In addition, a plurality of processing units may be configured by one processor.

A first example of the configuration in which the plurality of processing units are configured by one processor is a form in which one processor is configured by a combination of one or more CPUs and software and the processor functions as the plurality of processing units, as represented by the computer, such as a client and a server. Second, as represented by a system on chip (SoC) or the like, there is a form of using a processor that realizes the function of the entire system including the plurality of processing units by one integrated circuit (IC) chip. As described above, various processing units are configured by one or more of the various processors as the hardware structure.

Further, more specifically, an electric circuit (circuitry) obtained by combining circuit elements, such as semiconductor elements, can be used as the hardware structure of the various processors.

In addition, in the embodiment described above, an aspect has been described in which the learning program 51 and the image recognition program 52 are stored (installed) in the storage unit 43 in advance, but the disclosed technology is not limited to this. The learning program 51 and the image recognition program 52 may be provided in a form of being recorded in a recording medium, such as a compact disc read only memory (CD-ROM), a digital versatile disc read only memory (DVD-ROM), and a universal serial bus (USB) memory. In addition, a form may be adopted in which the learning program 51 and the image recognition program 52 are downloaded from an external device via the network.

It should be noted that the disclosure of JP2020-163872 filed on Sep. 29, 2020 is incorporated in the present specification in its entirety by reference. In addition, all documents, patent applications, and technical standards described in the present specification are incorporated herein by reference to the same extent as in a case in which each document, each patent application, and each technical standard are specifically and individually described by being incorporated in the present specification by reference.

What is claimed is:

1. An information processing apparatus comprising:
at least one processor,
wherein the processor
acquires a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images, calculates, for each first training image, a first evaluation value for training an estimation model such that the plurality of regions specified by using the estimation model match the area information, derives, for each second training image, estimation information in which the relationship indicated by the relationship information is estimated by using the estimation model to calculate a second evaluation value indicating a degree of deviation between the estimation information and the relationship information, and trains the estimation model such that a loss including, as elements, the first evaluation value and the second evaluation value is reduced.

2. The information processing apparatus according to claim 1, wherein the relationship between the plurality of regions is an inclusion relationship between the plurality of regions.

3. The information processing apparatus according to claim 2, wherein the plurality of training images each include a first region and a second region including at least a part of the first region, the relationship information is information indicating whether or not the first region has a portion that is not included in the second region in the second training image, and the estimation information is a probability that the first region has the portion that is not included in the second region in the second training image.

4. The information processing apparatus according to claim 3, wherein the processor calculates, for each pixel of the second training image, a probability $P_x$ that the pixel is a pixel of the portion of the first region that is not included in the second region by using the estimation model, and derives, as the estimation information, a value calculated based on the probability $P_x$ calculated for each pixel.

5. The information processing apparatus according to claim 3, wherein the training image is a medical image, and the first region is a lesion region and the second region is a biological tissue region including at least a part of the lesion region.

6. The information processing apparatus according to claim 3, wherein the processor acquires a target image including the first region and the second region, specifies at least one of the first region, the second region, or the portion of the first region that is not included in the second region by using the estimation model, and performs control of displaying the specified region or portion in a discriminable manner.

7. The information processing apparatus according to claim 1, wherein the relationship between the plurality of regions is a magnitude relationship between specific elements included respectively in the plurality of regions.

8. The information processing apparatus according to claim 7, wherein the plurality of training images each include a first region and a second region, the relationship information is information indicating whether or not the element in the first region is larger than the element in the second region in the second training image, and the estimation information is a probability that the element in the first region is larger than the element in the second region in the second training image.

9. The information processing apparatus according to claim 8, wherein the processor specifies, for each second training image, the first region and the second region by using the estimation model, derives a size $F_A$ of the element in the first region and a size $F_B$ of the element in the second region, and derives, as the estimation information, a value according to a difference between the size $F_A$ of the element in the first region and the size $F_B$ of the element in the second region.

10. The information processing apparatus according to claim 1, wherein the relationship between the plurality of regions is a positional relationship between the plurality of regions.

11. The information processing apparatus according to claim 10, wherein the plurality of training images each include a first region and a second region, the relationship information is information indicating whether or not the first region is located in a specific direction with respect to the second region in the second training image, and the estimation information is a probability that the first region is located in the specific direction with respect to the second region in the second training image.

12. The information processing apparatus according to claim 11, wherein the processor calculates, for each pixel of the second training image, a probability $P_a$ that the pixel is the first region and a probability $P_b$ that the pixel is the second region by using the estimation model, sets a candidate region located in the specific direction with respect to a pixel at an end portion on a side in the specific direction among pixels in which the probability $P_b$ is equal to or larger than a threshold value, and derives, as the estimation information, a value calculated based on the probability $P_a$ calculated for a pixel in the candidate region.

13. The information processing apparatus according to claim 1, wherein, in a case in which the second evaluation value is E2, the estimation information is $y_K$, and the relationship information is $t_K$, Expression (I) is satisfied $$E2=\Sigma\{-t_K \log y_K-(1-t_K)\log(1-y_K)\} \quad (I).$$

14. An information processing method executed by at least one processor provided in an information processing apparatus, the method comprising:

acquiring a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images;

calculating, for each first training image, a first evaluation value for training an estimation model such that the plurality of regions specified by using the estimation model match the area information;

deriving, for each second training image, estimation information in which the relationship indicated by the relationship information is estimated by using the estimation model to calculate a second evaluation value indicating a degree of deviation between the estimation information and the relationship information; and training the estimation model such that a loss including, as elements, the first evaluation value and the second evaluation value is reduced.

15. A non-transitory computer-readable storage medium storing an information processing program causing at least one processor provided in an information processing apparatus to execute a process comprising:

acquiring a plurality of first training data in which area information indicating an area in which each of a plurality of regions is present is added to a first training image which is at least a part of a plurality of training images each including the plurality of regions, and a plurality of second training data in which relationship information indicating a relationship between the plurality of regions is added to a second training image which is at least a part of the plurality of training images;

calculating, for each first training image, a first evaluation value for training an estimation model such that the plurality of regions specified by using the estimation model match the area information;

deriving, for each second training image, estimation information in which the relationship indicated by the relationship information is estimated by using the estimation model to calculate a second evaluation value indicating a degree of deviation between the estimation information and the relationship information; and training the estimation model such that a loss including, as elements, the first evaluation value and the second evaluation value is reduced.

* * * * *